(12) United States Patent
Steger

(10) Patent No.: US 7,556,460 B2
(45) Date of Patent: Jul. 7, 2009

(54) COPY MILLING DEVICE FOR MACHINING WORKPIECES, IN PARTICULAR FOR MILLING DENTAL WORKPIECES

(76) Inventor: Heinrich Steger, Giuseppe-Verdi-Strasse 18, Bruneck (IT) IT-39031

( * ) Notice: Subject to any disclaimer, the term of this patent is extended or adjusted under 35 U.S.C. 154(b) by 0 days.

(21) Appl. No.: 11/807,280

(22) Filed: May 25, 2007

(65) Prior Publication Data
US 2007/0237595 A1 Oct. 11, 2007

Related U.S. Application Data

(63) Continuation of application No. PCT/IB2005/004043, filed on Nov. 17, 2005.

(30) Foreign Application Priority Data

Nov. 25, 2004 (AT) .............................. A 1992/2004
Jun. 30, 2005 (AT) .............................. A 1104/2005

(51) Int. Cl.
*B23C 1/16* (2006.01)
(52) U.S. Cl. .............................. 409/89; 409/90; 409/88; 409/92; 409/137; 409/221; 269/58; 269/71; 269/909; 269/40; 269/287
(58) Field of Classification Search .................. 409/86, 409/87, 88, 89, 90, 92, 126, 109, 137, 85, 409/93, 94, 96, 107, 104, 111, 112, 125, 409/127, 165, 164, 163, 219, 221, 224, 225, 409/237; 269/47, 58, 71, 909, 40, 287
See application file for complete search history.

(56) References Cited
U.S. PATENT DOCUMENTS

| 361,131 A | 4/1887 | Carlinet | |
|---|---|---|---|
| 2,631,375 A | * 3/1953 | Gleason | ........................ 409/86 |
| 2,646,725 A | 9/1953 | Brynildsrud | |
| 3,100,344 A | * 8/1963 | Sharp | .......................... 409/86 |

(Continued)

FOREIGN PATENT DOCUMENTS

DE 7609941 U 6/1977

(Continued)

OTHER PUBLICATIONS

Merriam Webster's Collegiate Dictionary, 10$^{th}$ ed., copyright 1993, p. 334, definition of "disk".*

(Continued)

*Primary Examiner*—Erica E Cadugan
(74) *Attorney, Agent, or Firm*—Laurence A. Greenberg; Werner H. Stemer; Ralph E. Locher

(57) ABSTRACT

A copy milling device for the production of in particular dental workpieces, comprising a carrier plate for a model body and a shaping blank, an arm which is arranged pivotably about a horizontal axis extending substantially normal to its longitudinal direction and which has a motor-driven machining tool for cutting shaping of a workpiece from the shaping blank and a tracing device for tracing the model portion, wherein the machining tool and the tracing device are mechanically and synchronously movably connected, wherein the copy milling device comprises a suspension device for the arm.

50 Claims, 11 Drawing Sheets

U.S. PATENT DOCUMENTS

| | | | | |
|---|---|---|---|---|
| 3,276,122 | A | * | 10/1966 | Slayton ..................... 269/909 |
| 3,382,740 | A | | 5/1968 | Lotta |
| 3,453,933 | A | | 7/1969 | Kornhauser |
| 3,863,544 | A | * | 2/1975 | Reeber et al. ................. 409/89 |
| 4,458,736 | A | | 7/1984 | Trevor |
| 4,863,318 | A | * | 9/1989 | Pearl ........................... 409/89 |
| 5,135,393 | A | * | 8/1992 | Eidenbenz et al. .......... 409/124 |
| 5,342,696 | A | * | 8/1994 | Eidenbenz et al. .......... 269/287 |
| 5,383,752 | A | | 1/1995 | Rheinberger et al. |
| 6,101,666 | A | | 8/2000 | Cheng |
| 6,186,711 | B1 | | 2/2001 | Mueller |
| 6,454,568 | B1 | * | 9/2002 | Beuschel et al. ............. 433/163 |
| 6,641,340 | B1 | * | 11/2003 | Hajjar et al. .................. 409/94 |
| 6,905,293 | B1 | * | 6/2005 | Filser et al. ................... 409/84 |
| 7,077,391 | B2 | | 7/2006 | Filser et al. |
| 7,101,180 | B2 | | 9/2006 | Filser et al. |
| 7,234,938 | B2 | | 6/2007 | Bodenmiller |
| 2003/0132539 | A1 | | 7/2003 | Althoff et al. |
| 2004/0072121 | A1 | | 4/2004 | Filser et al. |
| 2008/0070186 | A1 | * | 3/2008 | Steger ......................... 433/75 |

FOREIGN PATENT DOCUMENTS

| | | |
|---|---|---|
| DE | 7835355 U1 | 5/1980 |
| DE | 370445 A1 | 8/1988 |
| DE | 19626174 C1 | 10/1997 |
| DE | 10114917 A1 | 10/2002 |
| DE | 10132986 A1 | 1/2003 |
| EP | 0030534 B1 | 12/1983 |
| EP | 0216983 A2 | 4/1987 |
| EP | 0384908 A2 | 8/1990 |
| EP | 0402720 A1 | 12/1990 |
| EP | 0543258 A2 | 5/1993 |
| EP | 0947355 A2 | 10/1999 |
| EP | 1245332 A1 | 10/2002 |
| GB | 576518 A | 4/1946 |
| GB | 667806 A | 3/1952 |
| WO | 9208420 A1 | 5/1992 |
| WO | 9530382 A1 | 11/1995 |
| WO | 9605781 A1 | 2/1996 |
| WO | 9605782 A1 | 2/1996 |
| WO | WO 01/97707 A1 | 12/2001 |
| WO | 0245614 A1 | 6/2002 |
| WO | 0247573 A1 | 6/2002 |

OTHER PUBLICATIONS

KaVo Everest engine 4140, Gebrauchsanweisung (Instruction Manual), published in 2003, Leutkirch im Allgäu, Germany Obs. The device shown in the non-patent literature roughly corresponds to the device shown in EP 1 245 332 A1 (corresp. U.S. Appl. 7,234,938) filed with information Disclosure Statement dated Aug. 13, 2008.
International Search Report dated Feb. 9, 2007.
Austrian Search Report dated Mar. 15, 2006.
Austrian Search Report dated Oct. 5, 2005.

* cited by examiner

COPY MILLING DEVICE FOR MACHINING WORKPIECES, IN PARTICULAR FOR MILLING DENTAL WORKPIECES

CROSS-REFERENCE TO RELATED APPLICATIONS

This is a continuation, under 35 U.S.C. § 120, of copending international application No. PCT/IB2005/004043, filed Nov. 17, 2005, which designated the United States; this application also claims the priority, under 35 U.S.C. § 119, of Austrian patent applications Nos. A 1992/2004, filed Nov. 25, 2004, and A 1104/2005, filed Jun. 30, 2005; the prior applications are herewith incorporated by reference in their entirety.

BACKGROUND OF THE INVENTION

Field of the Invention

The invention concerns a copy milling device for the production of workpieces, in particular dental workpieces. The device includes a carrier plate for a model body and a shaping blank, an arm which is arranged pivotally about a horizontal axis extending substantially normal to its longitudinal direction and which has a motor-driven machining tool for cutting shaping of a workpiece from the shaping blank and a tracing device for tracing the model portion. The machining tool and the tracing device are mechanically and synchronously movably connected.

The use of copy milling devices for the production of workpieces of a complicated three-dimensional shape has long been known. In that respect the shape of a model body is mechanically traced by way of a tracing device, the deflections of a tracing pin being transmitted synchronously to a motor-driven machining tool and the machining tool, in a cutting machining operation, for example by milling or grinding, machining a shaped body identical to the model body, from a shaping blank. In the case of large machine tools transmission of the deflections of the stylus is effected by means of a regulating device, but regulating devices of that kind are not required for the production of small shaped bodies, and for that reason the deflections of the stylus are transmitted directly to the machining tool and the stylus and the tool holder are mechanically fixedly coupled together.

For the production of dental workpieces such as for example inlays, onlays and crowns, besides the known filling materials such as dental amalgams and gold, oxide-ceramic materials which are distinguished by great hardness are being increasingly used. However working with such materials, for example zirconium, is comparatively complicated and expensive. Thus, when using green compacts or shaping blanks which have been subjected to intermediate sintering, sintering shrinkage which occurs in the terminate finishing sintering operation on the workpiece must already be taken into consideration. If in contrast shaping blanks which are already in the finished sintered condition are used, the copy milling procedure lasts for a correspondingly longer period of time because of the high level of hardness of the oxide-ceramic materials, and that in turn can lead to inaccuracies when using copy milling devices which are to be actuated manually. In that case very costly and complicated CAD/CAM systems are usually employed, the procurement of which however is financially scarcely viable for an individual dental laboratory or indeed an individual dentist.

SUMMARY OF THE INVENTION

It is accordingly an object of the invention to provide an inexpensive and simple copy milling device for workpieces which overcomes the above-mentioned disadvantages of the heretofore-known devices and methods of this general type and which can be operated manually and which even when involving complicated and thus time-intensive copy milling procedures allows exact reproduction of the model body.

According to the invention that object is attained by a suspension device for the arm, wherein a preferred embodiment provides that the suspension device has a spring for compensating for the weight of the arm, which acts between a support arranged above the arm on the copy milling device and the arm. That provides that the arm is held in a rest position by means of the spring so that the force to be applied by the user for moving the arm is kept as low as possible. Desirably in that respect the spring is connected to the arm in the portion of the arm which has the machining tool and the tracing device, preferably above the tracing device.

So that the spring always has the same force effect, irrespective of the horizontal position of the arm, or put more precisely the point of engagement of the spring on the arm, a further embodiment of the invention provides that the support for the spring is arranged horizontally movably on the copy milling device. A structurally simple solution is afforded in that respect when the support is mounted displaceably on a substantially horizontal holding device arranged on a vertical carrier. That therefore ensures that the support for the spring on the holding device can follow the point of engagement of the spring on the arm in the event of a reduction or increase in the length of the arm so that the spring remains oriented substantially vertically. In order to ensure that the spring remains oriented vertically even upon a pivotal movement of the arm about a horizontal axis which is substantially normal to the longitudinal direction of the arm the spring can be mounted in the engagement point on the arm movably, for example by means of a ball head.

A further embodiment of the invention provides that the arm is arranged pivotably about a vertical axis on the copy milling device. In that case it has proven to be desirable if the holding device is connected to the carrier pivotably about the longitudinal axis thereof so that the support of the spring on the holding device can follow the point of engagement of the spring on the arm even when the arm is pivoted about a vertical axis.

In accordance with a further embodiment of the invention that can also be achieved in that the fixing device for the support on the holding device has at least two mutually crossing linear guides.

The applicant's tests have shown that particularly easy-running and practical operability of the copy milling device according to the invention is achieved when the vertical spacing of the holding device from the carrier plate is between 15 cm and 60 cm, preferably about 35 cm, and the spring constant is between 5 N/m and 10 N/m, preferably being about 7.3 N/m.

A further variant of the invention which allows particularly accurate copying of the model body with the lowest possible level of application of force provides that the motor-driven machining tool is arranged or can be arranged accessibly for a user in the condition of use and has a gripping element by means of which the position of the machining tool and the tracing device mechanically connected thereto is variable.

In contrast to the previously known manual copy milling devices therefore the position of the machining tool is altered directly and the tracing device is trackingly controlled by way of the mechanical coupling. In other words, the machining tool functions as a master and the tracing device as a slave, whereas in the state of the art the tracing device functions as a master and the machining tool is moved indirectly by way of the mechanical coupling. With this arrangement according to the invention, not only is the force necessary for moving the machining tool kept lower, but also inaccuracies which can occur in the transmission of the movement from the tracing device to the machining tool are avoided.

As already mentioned hereinbefore the machining of shaping blanks in the finished sintered condition is complicated and expensive and tedious. A further embodiment of the invention provides that the mechanical connection between the machining tool and the tracing device includes a reducing and/or enlarging mechanism. Advantageously in that respect the step-down or step-up mechanism is formed by a pantograph. A copy milling device of such a nature provides that workpieces can be produced from green compacts which are substantially easier to machine or from pre-sintered shaping blanks, more specifically having regard to the sintering shrinkage which occurs in the subsequent finishing sintering operation.

As the shrinkage factor of oxide-ceramic materials is substantially dependent on the process for the production of the materials or the temperatures in the pre-sintering process, a preferred embodiment of the invention provides that the step-down ratio from the machining tool to the tracing device is between 1:0.9 and 1:0.7, so that adaptation of the copy milling device to different materials is possible in principle. Recently however oxide-ceramic materials, in particular zirconium, are also available on the market, in respect of which all shaping blanks always have the same shrinkage factor, for example 25%, for which reason a particularly preferred embodiment of the invention provides that the transmission ratio is about 1:0.8.

That affords totally new perspectives for the individual dentist or the individual dental laboratory. Production of the medical workpiece on the basis of a model body no longer has to be effected out-of-house, as was hitherto usual, but rather the individual dentist or the individual dental laboratory can easily produce the workpiece from a green compact which is easy to work or pre-sintered material in a copy milling process and then provide for finishing sintering of that produced workpiece in a furnace. The fact that now the complete production process for a dental workpiece can take place in the dental practice or in the dental laboratory affords an enormous saving in terms of cost and time.

In order to be able to also produce workpieces involving complicated three-dimensional shapes, the three movement options for the arm—rotation about a vertical axis, rotation about a horizontal axis and reduction in length—are not sufficient. In accordance with a further embodiment of the invention it is therefore provided that the carrier plate for the model body and the shaping blank is arranged rotatably about a substantially horizontal axis, preferably over an angle of 360°, on the copy milling device. In that case the arrangement of the carrier plate can be such that the position of the carrier plate is variable in steps or steplessly.

In accordance with a further variant of the invention it is provided that the model body and/or the shaping blank can be or are arranged in the carrier plate preferably rotatably by means of a preferably disk-shaped holding element so that, by virtue of the fact that the model body and the shaping blank are held rotatably in the carrier plate, the copy milling device has a total of five degrees of freedom, that is to say with the copy milling device according to the invention it is possible to operate in the same five planes as is possible with a conventional 5-axis milling cutter.

Distortion of the shaping blank or the model body can be avoided by virtue of the arrangement of the model body and/or the shaping blank in a disk-shaped holding element. In that respect, in accordance with a further embodiment, at least the model body is glued into a receiving opening in a disk-shaped holding element of plastic material, wherein the outline of the preferably milled receiving opening is adapted to the contour of the model body. At the same time arranging the shaping blank and the model body in a disk-shaped holding element together with the rotatable mounting of the carrier plate ensures accessibility to the shaping blank and to the model body respectively from all sides.

In accordance with a further embodiment of the invention—in per se known manner—the machining tool has a milling element and the tracing device has a tracing element. If the arm includes a reduction or enlargement mechanism, a further embodiment of the invention provides that the milling element and the tracing element are of the same shape at least in the portions wherein they come into contact with the model body and the shaping blank respectively, wherein the portion of the milling element is proportionally larger, between 10% and 40%, preferably about 25%, than the portion of the tracing element. The enlargement or reducing mechanism at the arm and the proportional enlargement of the milling element with respect to the tracing element provides overall for complete scaling of the workpiece in relation to the model body.

In order to be able also to machine undercut configurations more easily with the copy milling device according to the invention, a further embodiment of the invention provides that the tips of the milling element and the tracing element are of a substantially trapezoidal configuration in cross-section, with the taper being towards the shank.

In order to relieve the load on the spring of the suspension device when the copy milling device is out of use a further embodiment of the invention provides that the carrier for the holding device has a supporting element for the arm and/or magnets for releasably fixing the arm to the carrier are arranged in the arm and in the carrier. Therefore when the copy milling device is not in use the arm can be easily rested on the carrier.

In accordance with a further embodiment of the invention the copy milling device has a base plate, at the underside of which is arranged a rotary mechanism for rotation of the entire copy milling device about a vertical axis, so that the user of the copy milling device does not need to change his working position during the copy milling operation, even if he is machining the workpiece on all sides. In that respect a further embodiment of the invention provides that the rotary mechanism includes a rotary fitment and preferably at least one braking element so that on the one hand, with the seating position remaining the same, that arrangement always guarantees an optimum view onto the object to be milled, while on the other hand the braking elements lock the rotary movement and thus unwanted rotary motion of the assembly is prevented.

The copy milling device according to the invention is therefore distinguished by a base plate which is preferably rotatable about a vertical axis and on which an arm having a machining tool and a tracing device is horizontally and vertically pivotably arranged, wherein the arm is preferably in the form of a pantograph with a transmission ratio of about 1:0.8, and further a carrier which is arranged rotatably on the base plate and which has a holding device on which the support of a tension spring acting on the arm is horizontally movably arranged, as well as a carrier plate which is mounted rotatably about a horizontal axis and on which disk-shaped holding elements are arranged preferably rotatably about a vertical axis, for receiving at least one shaping blank and a model body.

Furthermore the invention aims to provide a method of operating a copy milling device which is to be guided manually, having a motor-driven machining tool and a tracing device which are mechanically coupled and synchronously movable. In that respect, in the case of the previously known methods, a model body is mechanically traced with the tracing device and the deflections of the tracing device are transmitted to the motor-driven machining tool.

In contrast the method according to the invention is distinguished in that the force necessary for the change in position of the machining tool and the tracing device respectively is at least partially directly applied to the motor-driven machining tool, whereby that affords more precise guidance of the machining tool.

A preferred embodiment of the method according to the invention provides in that respect that the force necessary for the change in position is applied partially at the machining tool and partially at the tracing device, thereby overall affording easier work for the user as he now works with both hands, in contrast to the state of the art.

The present invention further concerns a carrier plate for a copy milling device.

The carrier plate serves in that respect for fixing the shaping blank, for example by adhesive means. The model body is mostly also fixed to the carrier plate.

In order to prevent the dust which is produced when milling the shaping blank from hindering the working operation, a variant of the invention provides that the carrier plate has at least one through opening which is so arranged that the dust produced when milling the shaping blank can pass therethrough.

The measure according to the invention permits suction removal of the dust in the region of the underside of the carrier plate whereby the working operation which is taking place in the upper region of the carrier plate is not impeded.

By way of example it can be provided that the carrier plate has an opening which is adapted to receive the shaping blank. Fixing of the shaping blank can be effected by means of adhesive points.

It is particularly advantageous if it is provided that a—preferably disk-shaped—holding element can be releasably fixed to the carrier plate, wherein the holding element has the opening for the shaping blank. That measure makes it possible for the shaping blank to be mounted to the holding element outside the carrier plate and then permits the holding element together with the shaping blank to be fixed to the carrier plate.

Fixing of the holding element to the carrier plate can preferably be effected by two-part inserts. Those two-part inserts can be rotated about vertical axes, for example with a 90° pitch, and are fastened by means of two cone screws. In that respect the upper part of the insert is of such a configuration that the disk-shaped holding elements can be very rapidly changed by slightly loosening the two cone screws and rotating the upper portion through a few degrees.

When using separate holding elements it is possible that the at least one through opening is also provided on the holding element.

In order to ensure easy rotatability of the holding element about a vertical axis it can be provided for example that the holding element has a circular peripheral edge.

A structurally particularly simple possible way of producing a holding element according to the invention provides that the holding element is in the form of a ring, wherein the ring is traversed by two limbs in such a way that the inner region of the ring has three openings. In that case the central opening can serve for fixing the shaping blank. The two flanking openings form the through openings for the dust which is produced upon milling of the shaping blank.

The present invention also concerns a holding element for a carrier plate in accordance with the aforementioned kind, wherein the holding element has a receiving means for a shaping blank and a through opening.

The invention also concerns a copy milling device having a carrier plate of the aforementioned kind, wherein the copy milling device preferably has a suction removal device for the dust produced upon milling of the shaping blank.

Other features which are considered as characteristic for the invention are set forth in the appended claims.

Although the invention is illustrated and described herein as embodied in copy milling device for the production of in particular dental workpieces, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
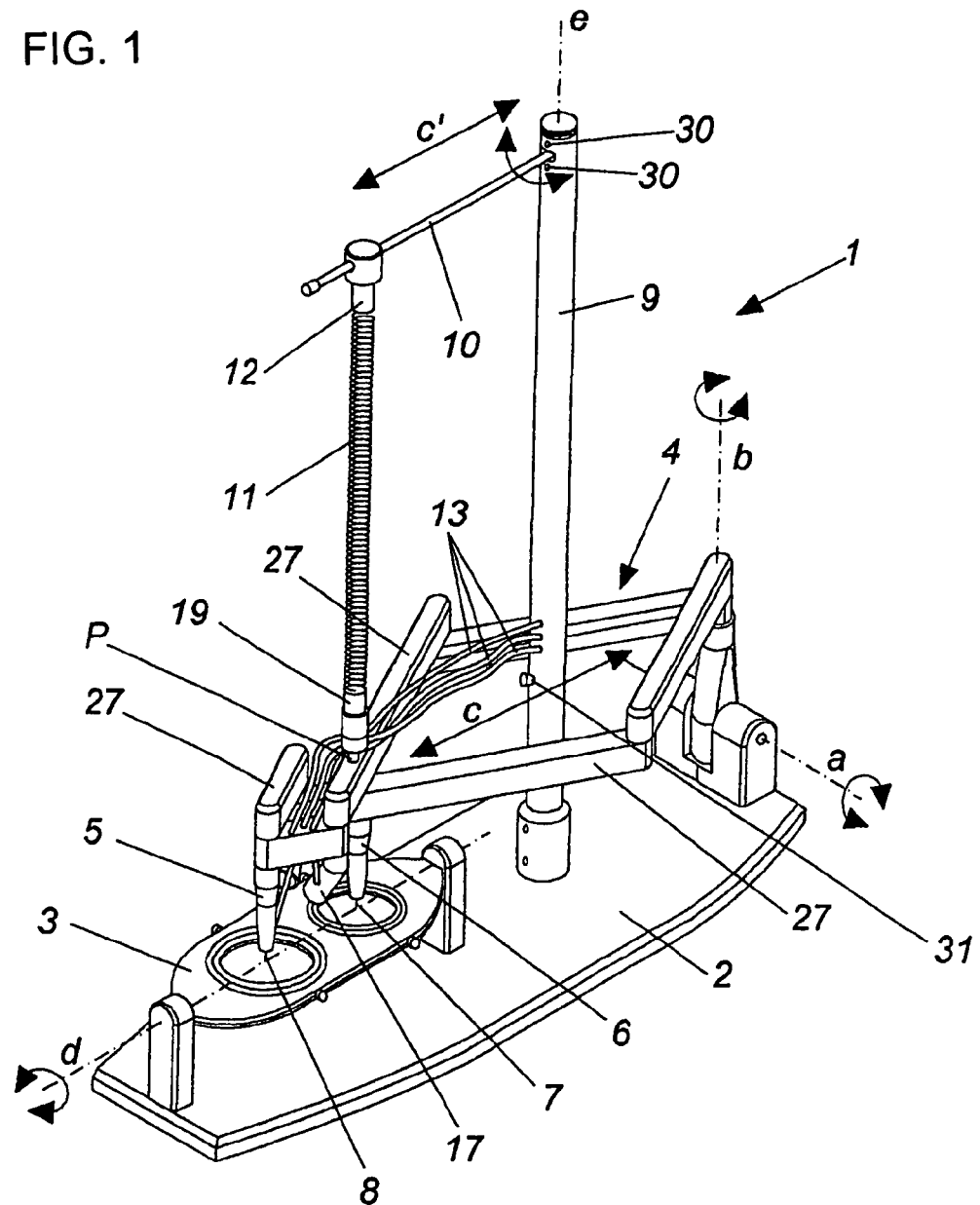
FIG. 1 shows a perspective view of an embodiment of the invention from above.
Figure 2:
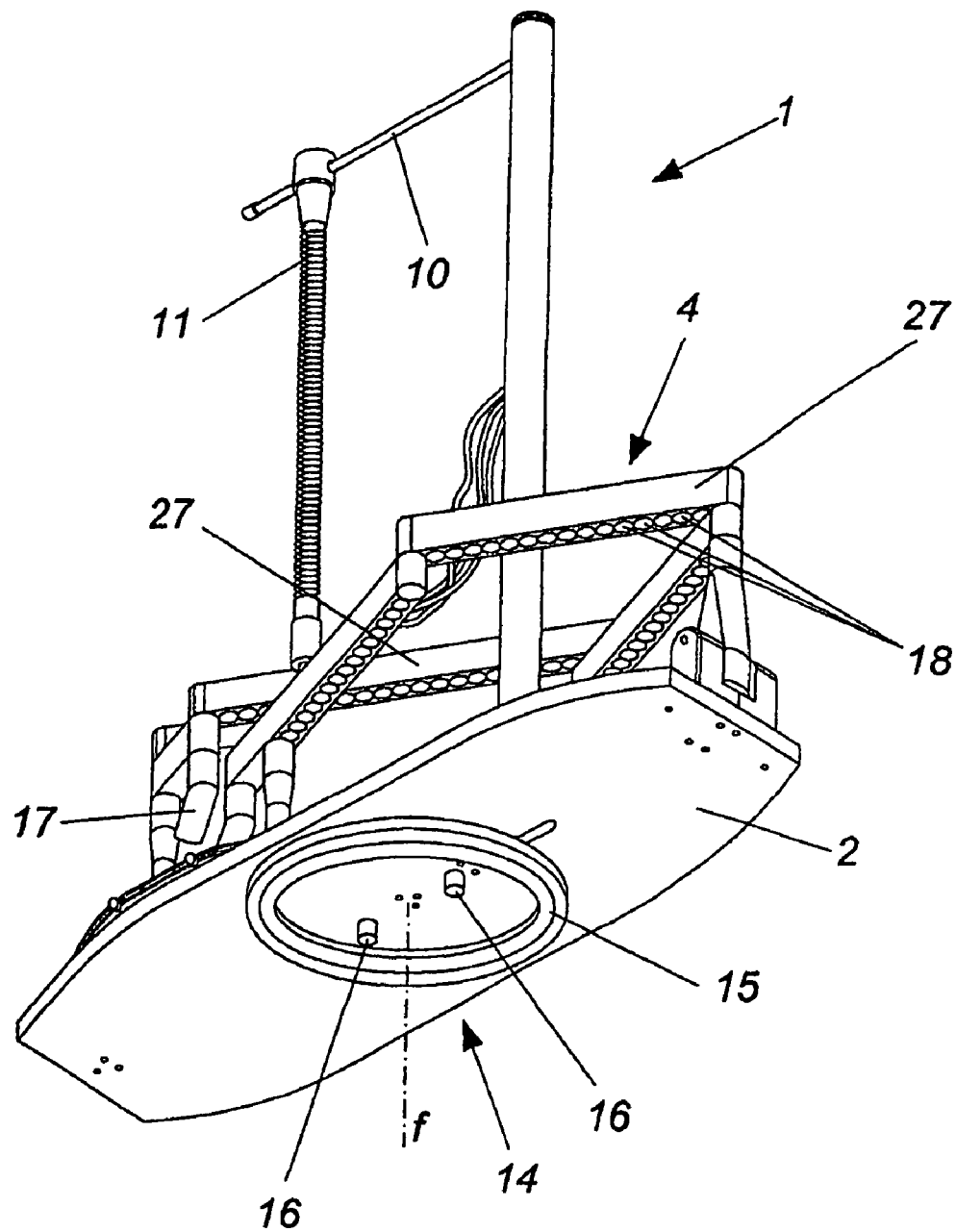
FIG. 2 shows a perspective view of an embodiment of the invention from below.
Figure 3C:
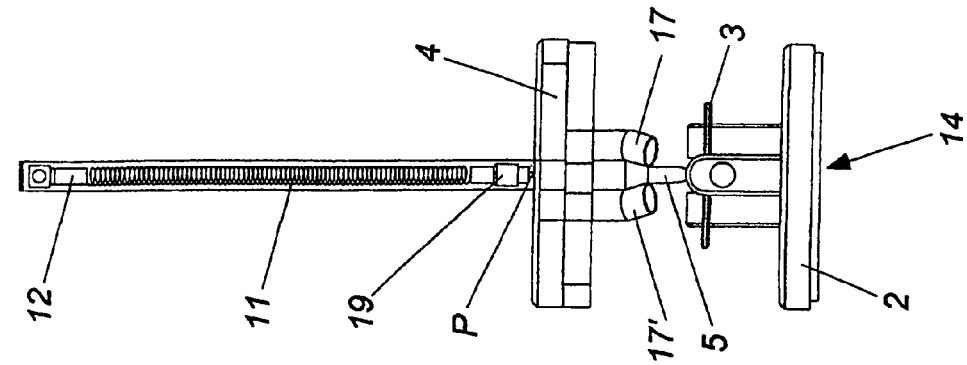
FIGS. 3a, 3b and 3c show a side view, a rear view and a front view of The copy milling device according to the invention.
Figure 3B:
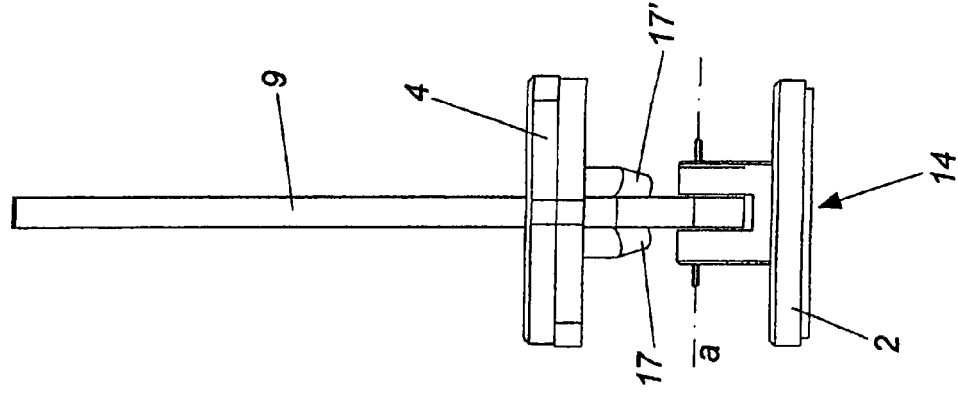
Figure 3A:
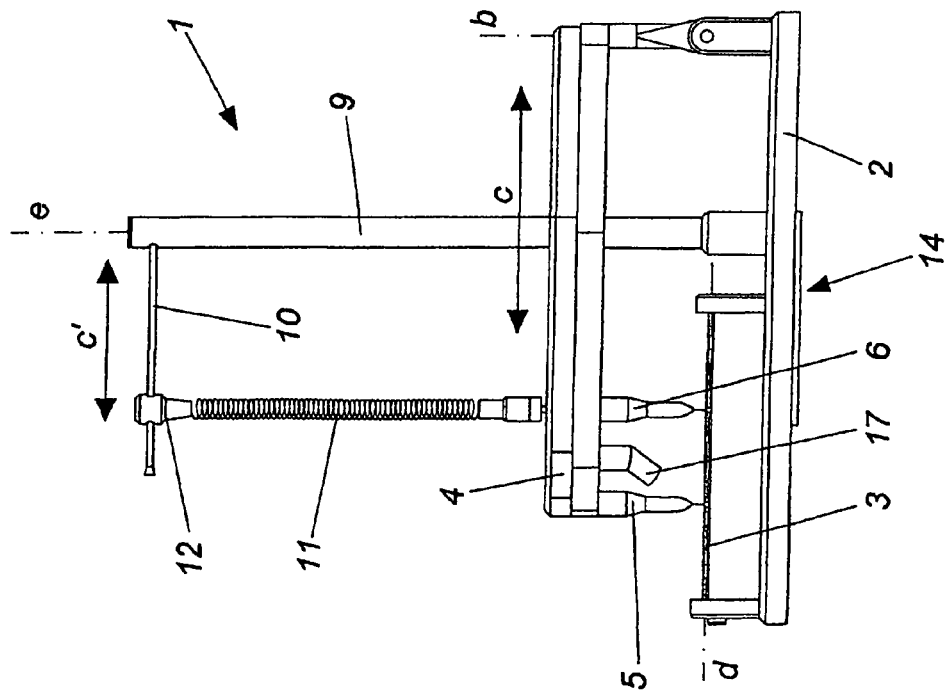

Referring now to the figures of the drawing in detail and first, particularly, to FIGS. 1-3 thereof, the embodiment of a copy milling device I according to the invention has a base plate 2, on the underside of which is arranged a rotary mechanism 14. The rotary mechanism 14 includes a rotary fitment 15 and braking elements 16. By virtue of the rotary fitment 15 it is possible for the copy milling device 1 to be rotated through 360° about a vertical axis and it is thus possible to ensure an optimum view onto the object to be milled while the operator is still remaining in the same sitting position. In other words, it is always possible to set an optimum viewing angle during a milling operation. The rotary movement is checked somewhat by the braking elements 16 so that unwanted rotary movement of the copy milling device 1 is prevented.

The arm 4 or jib or cantilever beam 4 is mounted on the base plate 2, preferably at the edge thereof. The arm 4 can be pivoted about a horizontal axis a substantially normal to the longitudinal direction of the arm 4 and about a vertical axis b. The arm 4 has a plurality of rotatably hingedly interconnected levers 27, the arrangement of which corresponds to what is referred to as a pantograph. Arranged on the arm 4 on the side of the arm 4 that is towards the base plate 2 of the copy milling device 1 are a motor-driven machining tool 5 and a tracing device 6. The configuration of the arm 4 in the form of a pantograph affords a step-up ratio of about 25% between the movement of the tracing device 6 and the motor-driven machining tool 5. Besides the two rotary movements about the axes a and b, the arm 4 can additionally be shortened or increased in length in the longitudinal direction c so that the arm 4 can be moved substantially in three directions.

Also arranged on the base plate 2 is a vertical carrier 9, at the end of which that is remote from the base plate 2 a holding device 10 for a support 12 for a spring 11 is substantially horizontally mounted. In that arrangement the holding device 10 can be pivoted about the longitudinal axis e of the carrier 9. The support 12 for the spring 11 is mounted to the holding device 10 displaceably in the longitudinal direction c' of the holding device 10. That ensures that the support 12 of the spring 11 can follow the point of engagement of the spring 11 on the arm 4 upon horizontal changes in the position of the arm 4 so that the spring 11 is substantially vertically oriented throughout the entire milling operation. In order to permit easy sliding movement of the support 12 on the holding device 10 the holding device 10 can be oriented horizontally by means of clamping screws 30.

In order to be able to vary the required application of force during the milling operation, it is possible by means of a rotatable sleeve 19 to increase the stress of the spring 11 or to reduce it and thus to set the rest position of the arm 4 higher or lower.

The carrier 9 is positioned on the base plate 2 in such a way that it does not hinder the user of the copy milling device 1 during his work. In addition the carrier 9 is hollow so that lines 13 can be guided in the carrier 9 whereby the copy milling device 1 can be rotated about its axis without involving entanglement of the lines 13. In that respect the lines 13 can include power supply cables for the motor-driven machining tool 5 or the lighting elements 17. However air lines which aspirate the milling dust away from the working location or blow it away can be guided in the carrier 9 without any problem.

Thus the copy milling device can have an air feed device, by means of which a slightly increased pressure is always produced in the interior of the machining tool. That increased pressure prevents particles of dust from being able to pass into the drive, in particular into the bearing configuration of the drive, of the machining tool. Advantageously a far higher air pressure which serves for blowing off the object to be milled can be supplied if required by way of that air feed device by means of a bypass line and a foot-actuated valve. If that high air pressure were to be continuously present, that would entail a very high level of dust production, which would make it difficult to aspirate the milling dust away. For the purposes of adaptation in accordance with the respective requirements involved, both the low ongoing pressure and also the high blow-off pressure can be adjusted by way of a pressure regulator individually and independently of the air pressure prevailing in the air feed device.

In addition, mounted to the carrier 9 is a supporting element 31 for the arm 4 in order to hold the arm 4 in a fixed position on the carrier 9. In addition, magnets can be arranged on the arm 4 and/or on the carrier 9 in the region of the supporting element 31, which assist with holding the arm 4 on the carrier 9.

As can be seen from FIG. 2 the levers 27 of the arm 4 have cavities 18. The purpose of this is to minimize the weight of the arm 4 in order in that way to be able to use a spring 11 having a low spring constant, which results in easy operation of the copy milling device 1. The applicant's tests have shown that optimum compensation for the weight of the arm 4 is afforded when the spring constant of the spring 11 is about 7.3 N/m.

Figure 4:
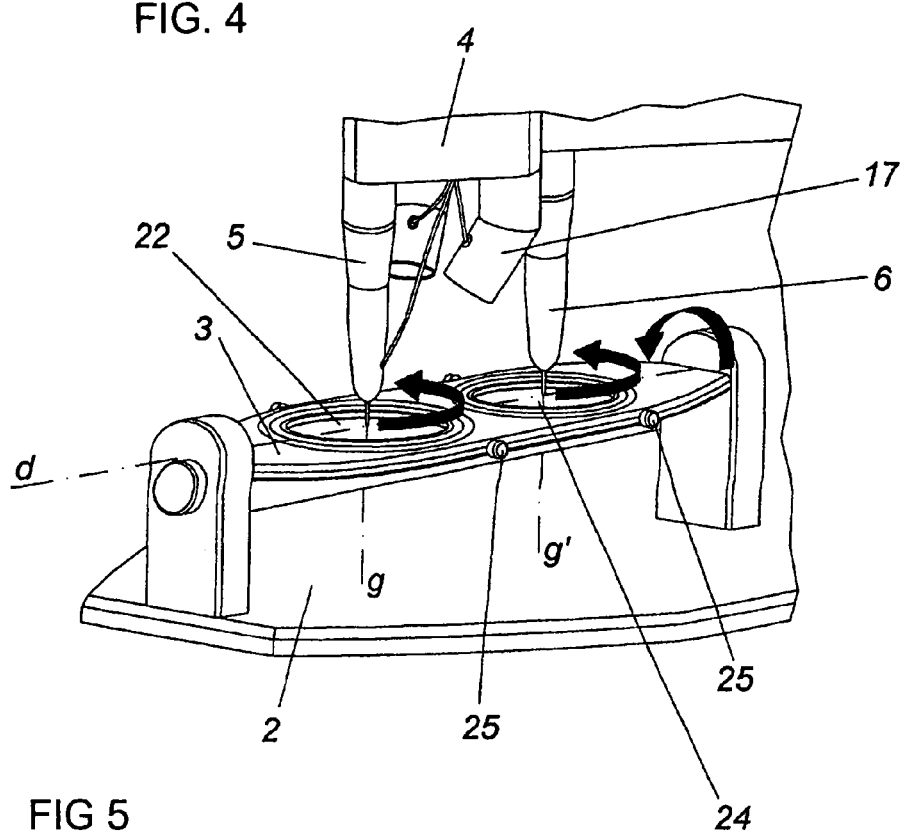
FIG. 4 shows a perspective view of the carrier plate and a part of the arm.

Furthermore a carrier plate 3 which is adapted to receive the model body and the shaping blank is arranged on the base plate 2, being mounted rotatably about a horizontal axis d. As can be seen from FIG. 4 the carrier plate 3 can be rotated through 360° about the horizontal axis d. In the illustrated embodiment the carrier plate 3 can be blocked every 30° by way of a cone (not shown). That rotatability of the carrier plate 3 makes it possible to produce undercut configurations without any problem.

The model body 21 and the shaping blank 20 respectively are mounted rotatably about vertical axes g, g' in the carrier plate 3 by way of disk-shaped holding elements 22, 24. By virtue of that specific mounting configuration in respect of the carrier plate 3 and the disk-shaped holding elements 22, 24 it is possible for the model body and the shaping blank to be rotated about two mutually normal axes. Together with the three directions of movement that are available to the arm 4, the copy milling device according to the invention therefore embraces a total of five axes of movement.

Figure 5:
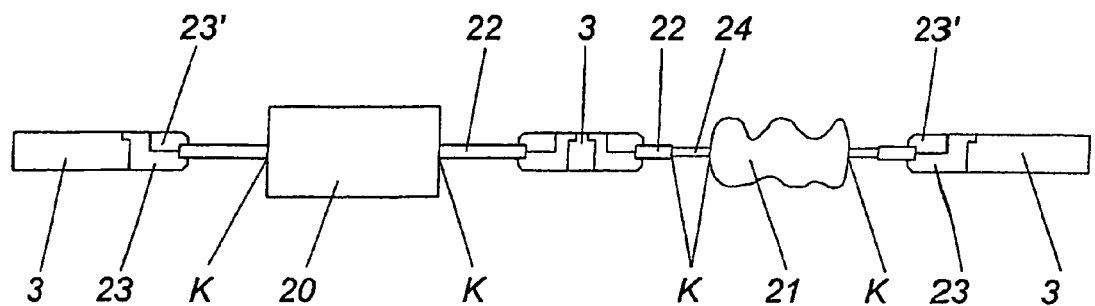
FIG. 5 diagrammatically shows the arrangement of the shaping blank and the model body in the carrier plate.

FIG. 5 diagrammatically shows the arrangement of the shaping blank 20 and the model body 21 in the carrier plate 3. In this case the model body 21 and the shaping blank 20 are gripped in position by being glued in disk-shaped holding elements 22 and 24 respectively. The gluing placement provides that no stress effects are transmitted to the shaping blank 20 and the model body 21 respectively. The holding element 22 for the shaping blank 20 is a prefabricated aluminum part while the holding element 24 for the model body 21 is produced from a millable plastic material, thereby providing for optimum rapid fixing of the model body 21. The model body 21 and the shaping blank 20 are fixed to the holding elements 22 and 24 by being glued fast at the adhesive points K.

Fixing of the holding elements 22 and 24 respectively in the carrier plate 3 is effected by means of two-part inserts 23, 23'. Those two-part inserts 23, 23' can be rotated about the vertical axes g, g' for example with a 90° pitch, and are fixed by means of two cone screws. In that respect the upper part of the insert 23' is of such a configuration that the disk-shaped holding elements 22 and 24 respectively can be very quickly exchanged by slightly loosening the two cone screws 25 and rotating the upper part 23' through a few degrees.

While the disk-shaped holding element 22 for the shaping blank 20 can be made from aluminum, it has proven to be advantageous for the disk-shaped holding element 24 for the model body 21 if that holding element 24 is made from millable plastic material. In that respect the plastic disk is firstly glued into an aluminum disk, afterwards the required opening in the holding element 24 for the model body 21 is milled out and then the model body 21 is glued in the holding element 24, for example by means of quick-setting adhesive. Although it would not be necessary for the holding element 24 of plastic material to be glued into a holding element 22 of aluminum, that measure has proven to be advantageous because it means that the holding element 24 of plastic material can be kept smaller and is thus more stable.

Figure 6:
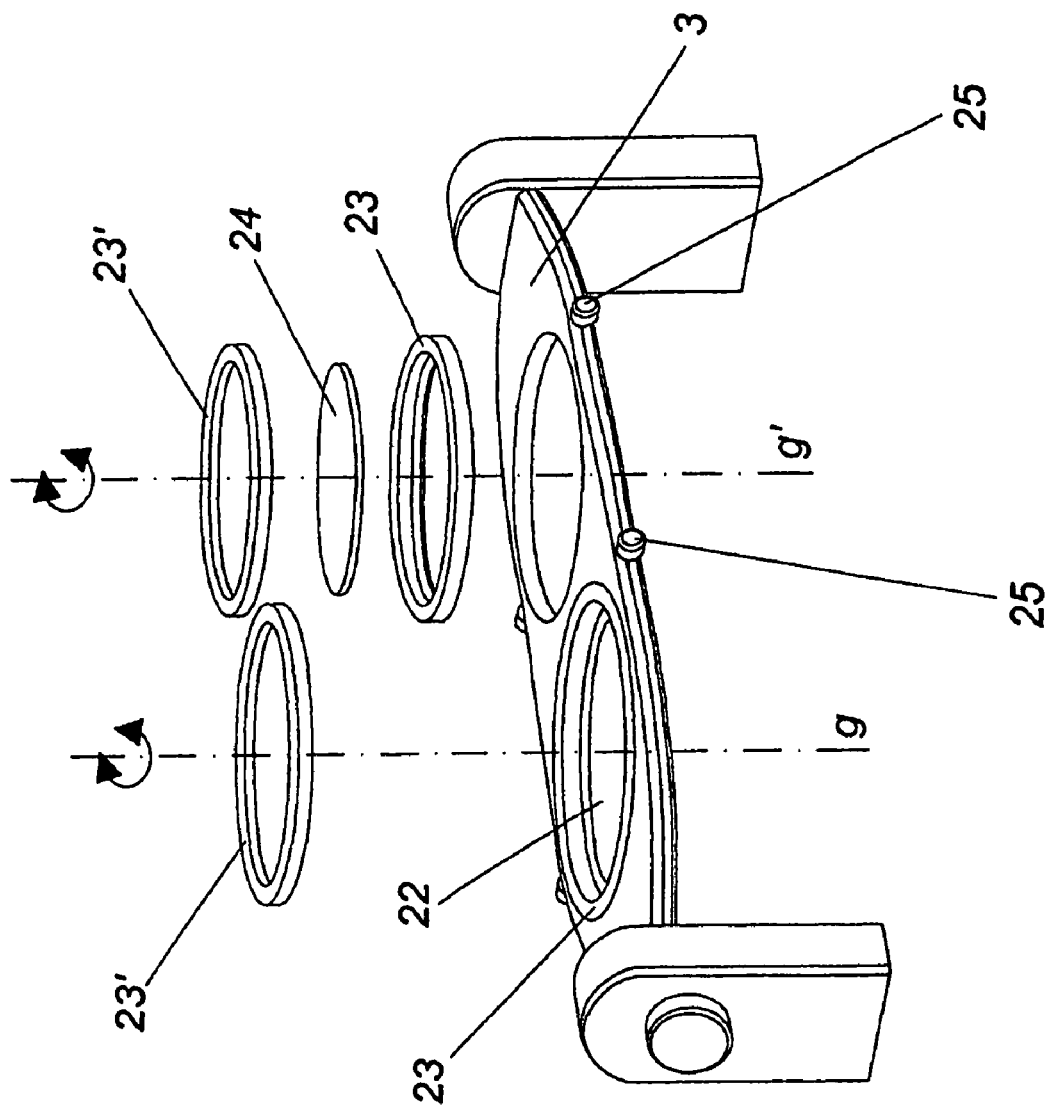
FIG. 6 shows the principle of the arrangement of the holding elements in the carrier plate.

FIG. 6 shows an exploded view illustrating the arrangement of the holding elements 22 and 24 in the carrier plate 3. In this case firstly the lower part 23 of the two-part insert is fitted into the through opening in the carrier plate 3. That is then followed by the holding elements 22 and 24 respectively which are now clamped fast with the upper part 23 of the two-part insert. The two-part inserts 23, 23' can be rotated about the vertical axes g, g' as already mentioned, and fixed by means of the cone screws 25.

Figure 7:
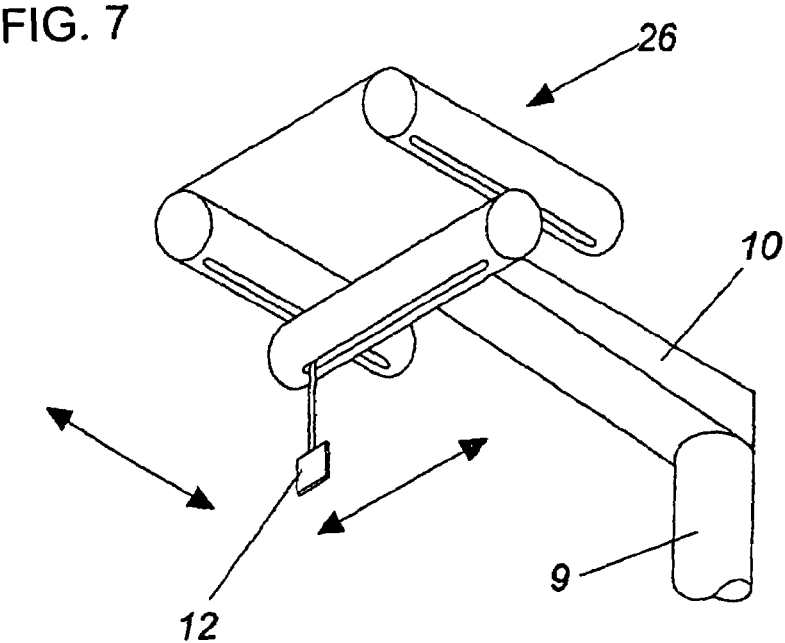
FIG. 7 shows a further embodiment of a holding device for the support for the spring on the suspension device.

FIG. 7 shows a further possible way of arranging the support 12 for the spring 11 horizontally movably on a holding device 10. In this embodiment the holding device 10 is rigidly connected to the carrier 9 but has a fixing device 26 for the support 12. In this case the fixing device 26 has two mutually crossing linear guides so that the support 12 can again follow the horizontal movements of the point of engagement P for the spring 11 on the arm 4.

Figures 8, 9A, 9B:
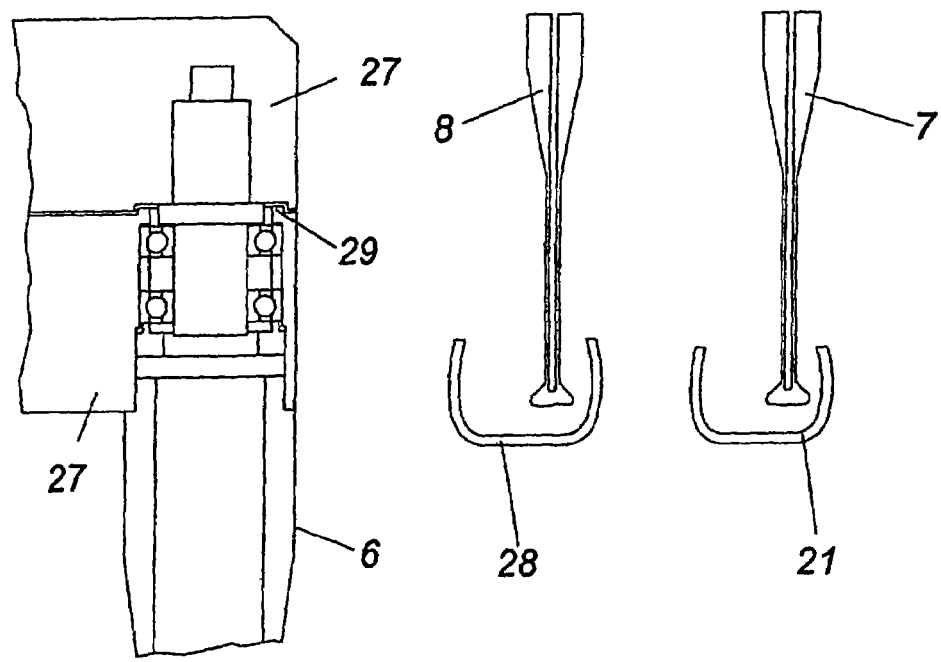
FIG. 8 shows the mounting concept of two movably interconnected levers of the arm.
FIGS. 9a and 9b show an embodiment for a milling element and a tracing element.

FIG. 8 shows the mounting concept in respect of two levers 27 of the arm 4. In contrast to the state of the art which generally uses a so-called fork mounting arrangement, in the case of the copy milling device 1 according to the invention a one-sided mounting configuration was designed, which affords the advantage that the levers 27 can be substantially smaller, which ensures optimum handling of the arm 4 in the milling procedure. The mounting unit itself comprises two bearings, a spacer bush and a shaft. In this arrangement the bearings are glued in a slightly prestressed condition on the shaft so that in the event of damage the mounting unit can be easily replaced as it only has to be mounted from one side. In order to prevent milling dust from penetrating into the mounting unit protective noses 29 were arranged on the lower lever and engage into the upper lever.

FIGS. 9*a* and 9*b* show a milling element 8 and a tracing element 7. In order to achieve complete scaling of the dental workpiece 28 in relation to the shaping blank 21, not only must the arm have a transmission ratio, but also the milling cutter-tracing device combination used must involve the same parameter relationship. In the illustrated embodiment the milling cutter is 25% larger, both in diameter and also the radii, than the tracing member. Undercut configurations can be produced without any problem by virtue of the special trapezoidal shaping of the tips of the milling element 8 and the tracing element 7. It should also be noted in this connection that a distinction is fundamentally drawn between finishing milling cutters and roughing milling cutters. While in the case of finishing milling cutters the relationship of the milling cutter to the tracing member must be exactly adapted to the transmission ratio of the arm, in the case of roughing milling cutters the milling cutter is somewhat smaller in order still to have residual material available for the subsequent finishing machining operation.

The milling element 8 and the tracing element 7 are glued in a receiving means and precisely matched to the same placement gripping length. In that way milling element and tracing element replacement is possible without a tedious operation of matching lengths. To achieve an optimum tool-quick-change system the milling elements and the tracing elements are matched to the same length, wherein case the milling element 8 and the tracing element 7 are clamped by means of a quick-action collet chuck. In that case the manner of mounting the spindles of the motor-driven machining tool 5 and the tracing device 6 is so selected that the holding configuration is kept as short as possible in order to reduce vibration to a minimum. That is achieved with the copy milling device 1 according to the invention by the spindles being screwed to the underside of a lever 27.

Likewise the two light sources 17 of the copy milling device 1 are fixed directly to the underside of the levers 27, thereby ensuring optimum illumination for the workpiece in any position as the light cone of the light source always follows the milling element 8.

Figure 10:
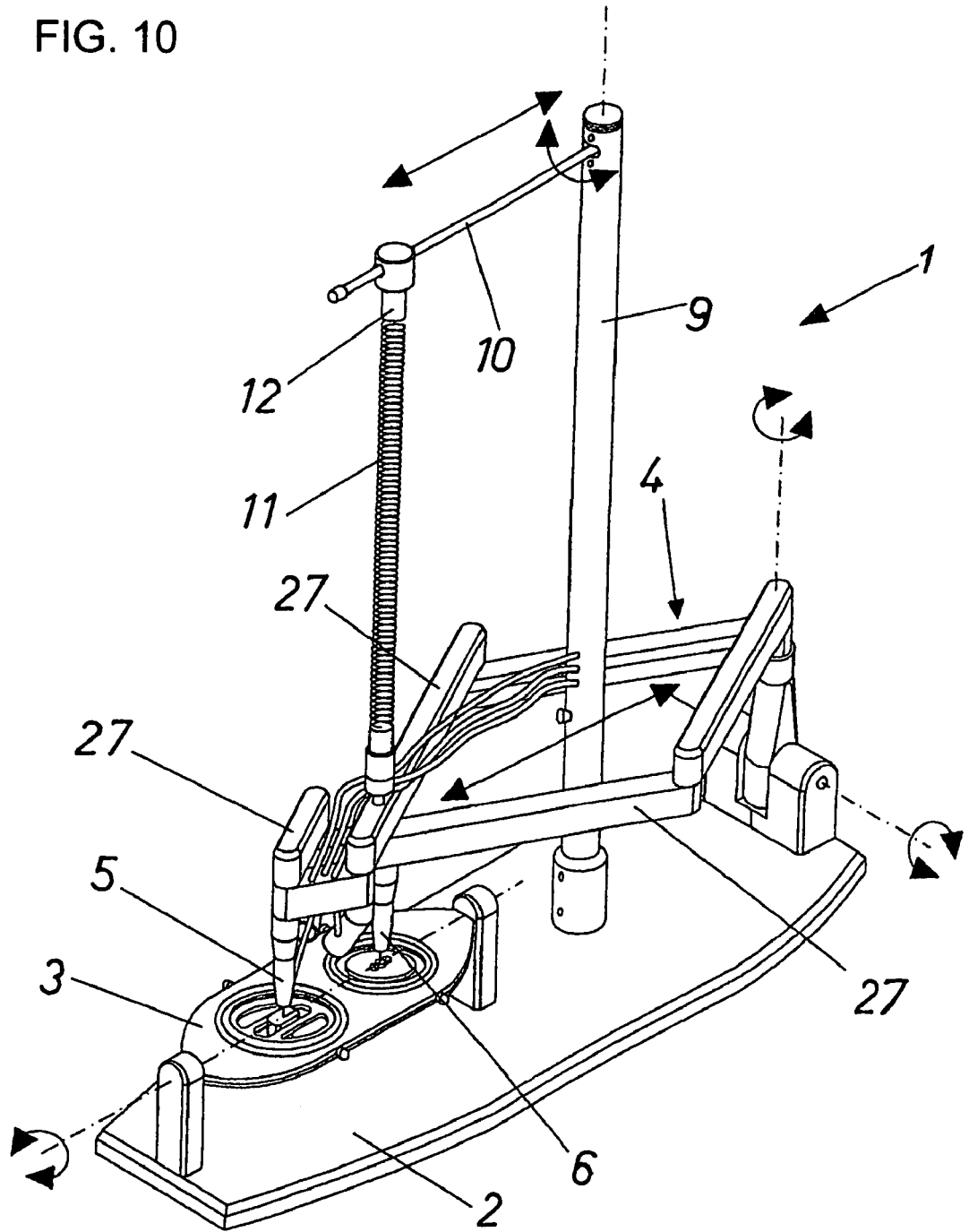
FIG. 10 shows a perspective view of a further variant of the invention.

FIG. 10 diagrammatically shows a further variant of a copy milling device 1, showing in particular the carrier plate 3. Arranged on a base plate 2 is a vertical carrier 9 on which a support 12 for a spring 11 is mounted by way of a holding device 10. The support 12 is mounted to the holding device 10 displaceably in the longitudinal direction of the holding device 10. That ensures that the support 12 of the spring 11 can follow the point of engagement of the spring 11 on the arm 4 upon changes in position so that the spring 11 is substantially vertically oriented throughout the entire milling operation. A motor-driven machining tool 5 for milling the shaping blank 20 and a tracing device 6 for tracing the model body are arranged by way of a pantograph-like arrangement of levers 18 which are pivotably connected together.

Figure 11A:
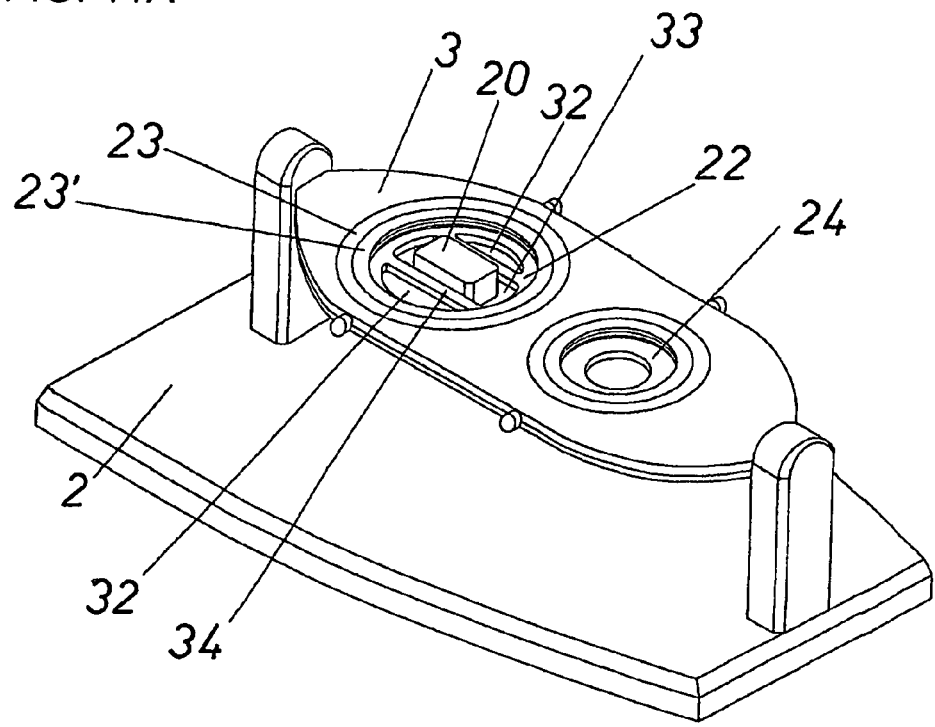
FIGS. 11a and 11b show detail views of The carrier plate according to the invention with a shaping blank fixed thereto.
Figure 11B:
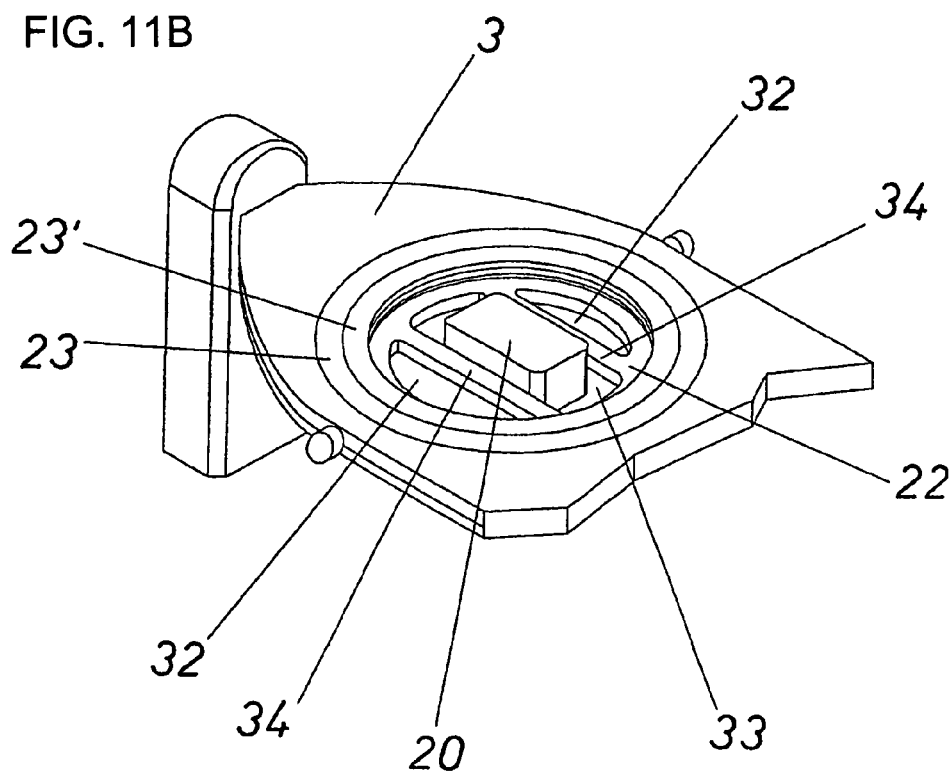
Figure 12B:
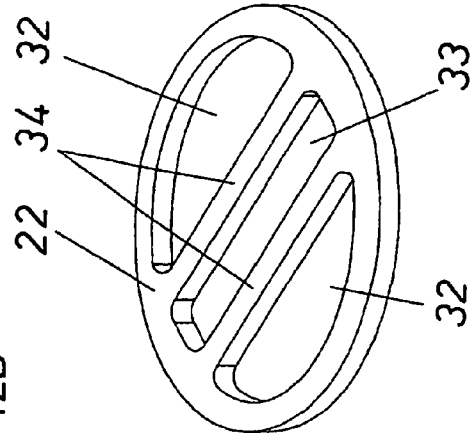
FIGS. 12a-12d show embodiments by way of example of holding elements of different configurations.
Figure 12D:
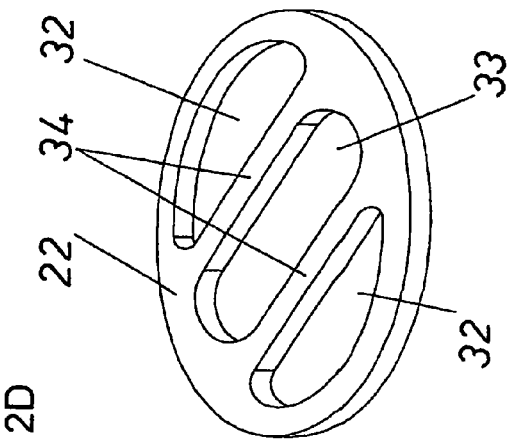
Figure 12A:
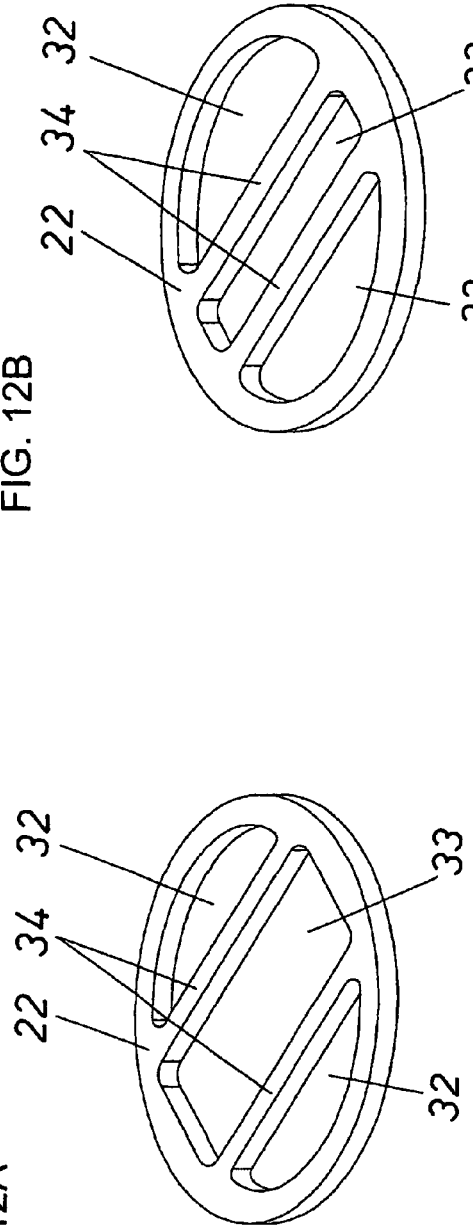
Figure 12C:
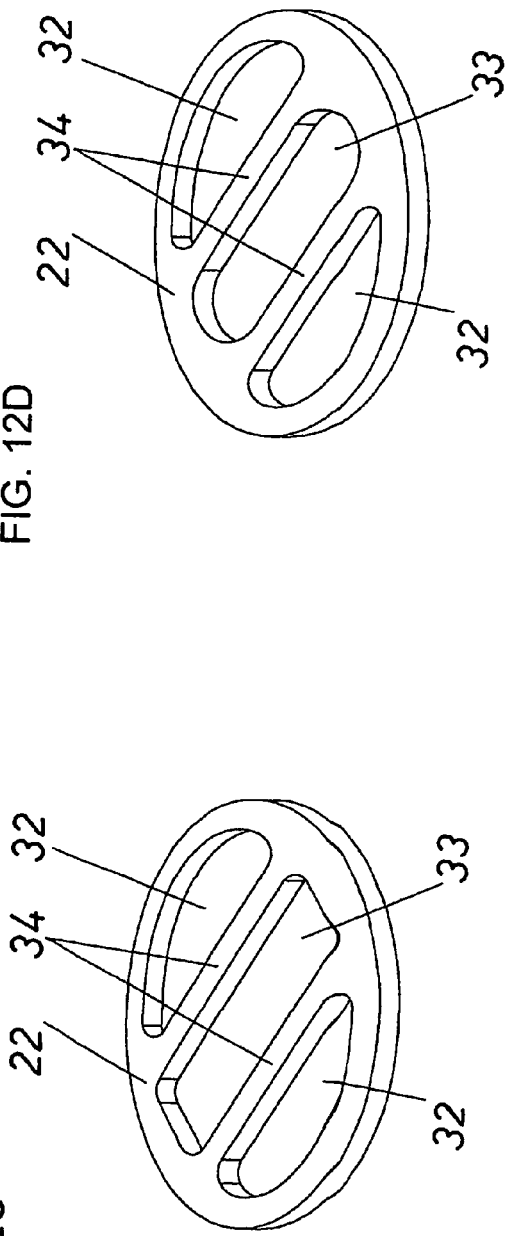

FIGS. 11*a* and 11*b* show detail views of the carrier plate 3 according to the invention at different degrees of magnification. It will be seen that the carrier plate 3 has a holding element 22 for a shaping blank 20, wherein the holding element 22 is fixed to the carrier plate 3 by means of two-part inserts 23, 23'. The shaping blank 20 is fixed to the limbs 34 of the holding element 22 by adhesive points. The figures clearly show the through openings 32 which are arranged at both sides of the shaping blank 20 and through which the dust produced when milling the shaping blank 20 can pass through the carrier plate 3 in the direction of the base plate. It is also possible to see that a model body (not shown in FIGS. 2*a* and 2*b*) can be fixed to the carrier plate 3 at a further holding element 24. As no dust is produced in the region of the model body, there is no need for the holding element 24 to be provided with through openings 32.

Various possible options in regard to the configuration of the holding element 22 are to be found in FIGS. 12*a* through 12*d*. The most widely varying shaping blanks can be arranged on the holding element 22, by virtue of the different design options involved. It will be seen that in each case a holding element 22 in the form of a circular ring has been adopted, wherein two limbs 34 extend in such a way that the interior of the circular ring has three openings 32, 33. In each case the shaping blank can be fixed in the central opening 33. The through openings 32 serve for carrying away the dust produced in the milling operation.

The shape of the holding element 22 is not restricted to the shape shown in FIGS. 12*a* through 12*d*. Although the configuration illustrated in FIGS. 12*a* through 12*d*, with a circular peripheral edge, is particularly advantageous by virtue of the ease of rotatability in the plane of the carrier plate 3, in principle it is also possible to conceive of different configurations such as for example with a polygonal peripheral edge.

Figure 13:
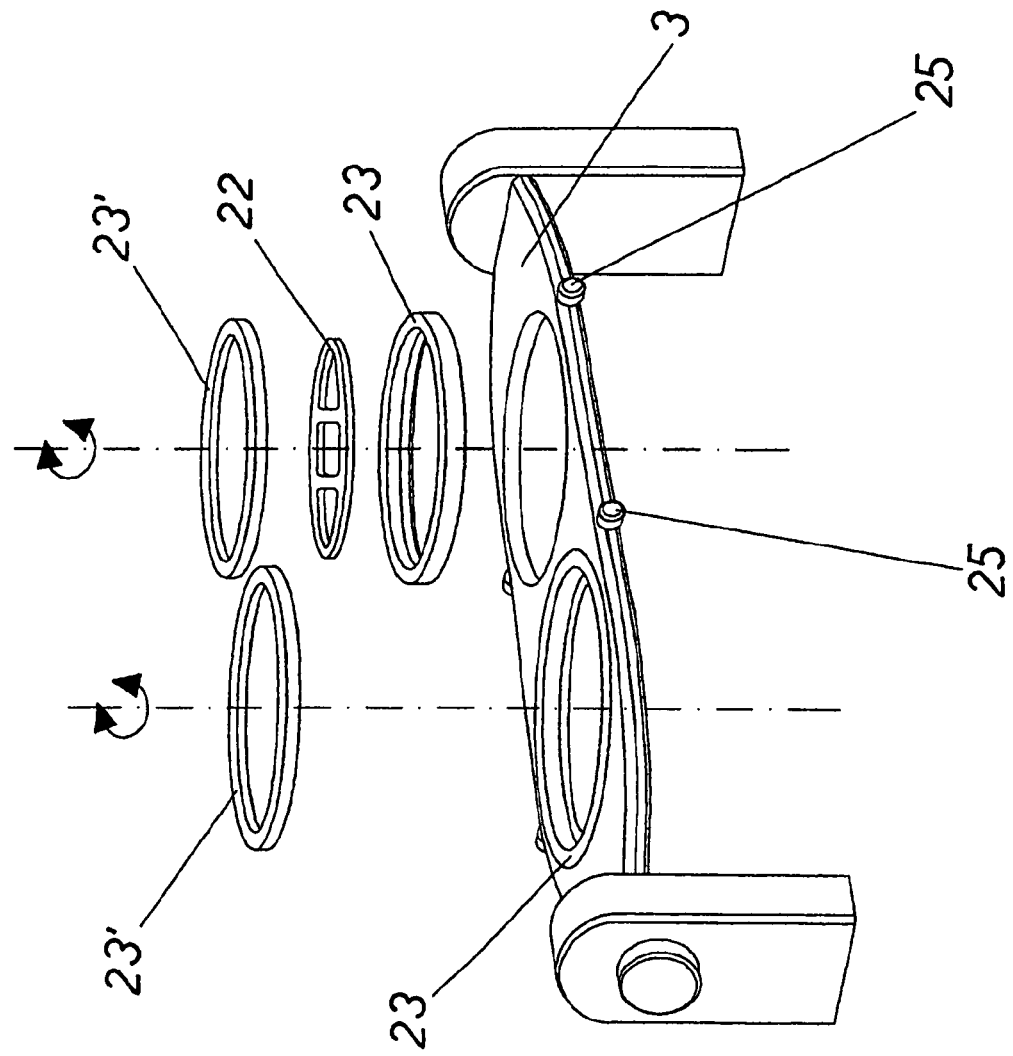
FIG. 13 shows an exploded view of The carrier plate according to the invention with two-part inserts.

FIG. 13 which illustrates an exploded view shows the fixing of the holding element 22 to the carrier plate 3 by means of the two-part inserts 23, 23'. In this case, firstly the lower part 23 of the two-part insert 23, 23' is fitted into the through opening in the carrier plate 3. That is then followed by the holding element 22 which is clamped fast with the upper part 23' of the two-part insert 23, 23'. The two-part inserts 23, 23' can be rotated about the illustrated vertical axis and fixed by means of the cone screws 25. A further through opening for a holding element 24 (not shown) for the model body can be seen on the left-hand side in FIG. 13. That holding element 24 can also be fixed to the carrier plate 3 by way of the two-part inserts 23, 23'.

The holding element 22 for the shaping blank 20 can be produced for example from aluminum. It has been found to be advantageous for the holding element 24 for the model body to be produced from millable plastic material. In that case firstly the plastic disk is glued into an aluminum disk, afterwards the required opening in the holding element 24 for the model body is milled out and the model body is glued in the holding element 24 for example by means of quick-setting adhesive.

Figure 14:
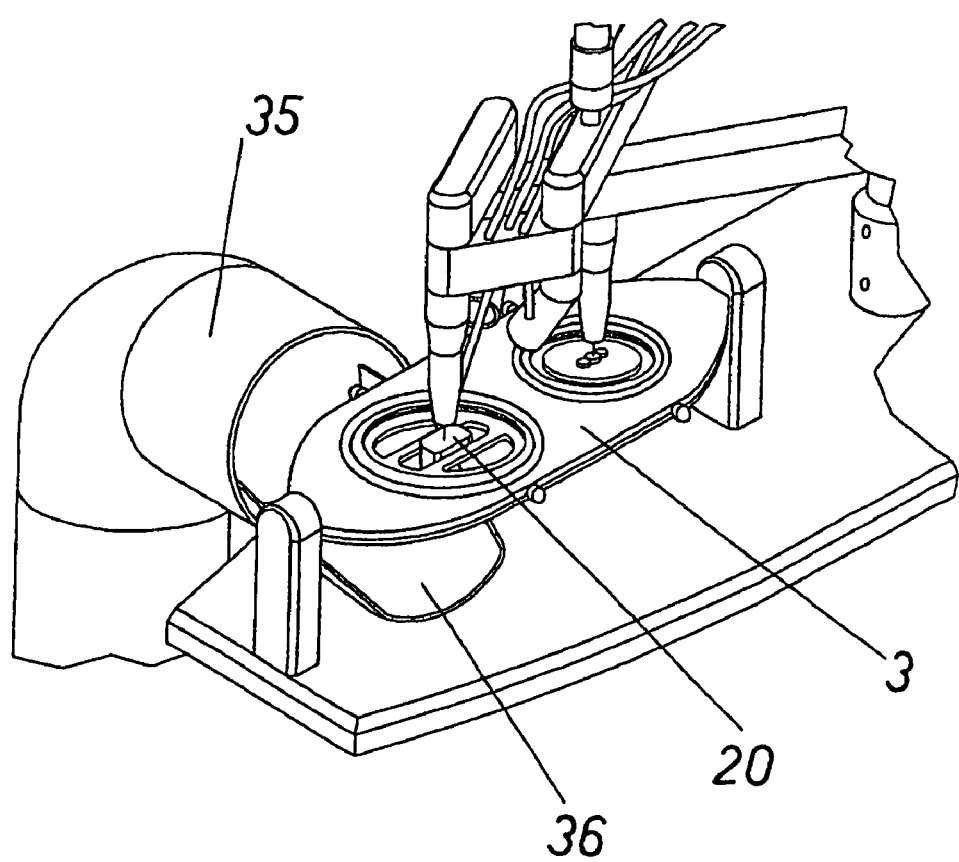
FIG. 14 shows a partial view of a copy milling device with a suction removal device.

FIG. 14 diagrammatically shows the arrangement of a suction removal device 35 for removing the dust produced when milling the shaping blank 20. In that case the dust can pass through the through openings 32 through the carrier plate 3 and is caught by a preferably arranged metal sheet 36 and removed by means of the suction removal device 35.

It will be appreciated that the illustrated embodiments of a mechanical copy milling device as well as the described example of a possible method of operating such a copy milling device are not to be interpreted in a restrictive sense but are only to be viewed as individual examples of numerous possible ways of implementing the concept of the invention of a mechanical copy milling device which is to be actuated manually.

The invention claimed is:

1. A copy milling device for milling workpieces, the device comprising:
    a carrier plate for supporting a model body and a shaping blank;
    an arm pivotally mounted about a horizontal axis extending substantially perpendicularly to a longitudinal direction of the arm;
    said arm carrying a motor-driven machining tool for machining a workpiece from the shaping blank and a tracing device for tracing the model body, said machining tool and said tracing device being mechanically connected and movable in synchronicity; and
    a suspension device for said arm, said suspension device including a spring for compensating for the weight of the arm, said spring connecting said arm and a support that is mounted so as to be horizontally movable relative to the carrier plate.

2. The copy milling device according to claim 1, wherein support is disposed above said arm.

3. The copy milling device according to claim 1, wherein said suspension device is connected to said arm at a portion of said arm that carries said machining tool and said tracing device.

4. The copy milling device according to claim 3, wherein said spring is connected to said arm above said tracing device.

5. The copy milling device according to claim 1, wherein said support for said spring that is mounted movably in a horizontal direction on the copy milling device enables a longitudinal axis of the spring to remain substantially vertical regardless of changes in a horizontal position of the arm.

6. The copy milling device according to claim 1, which comprises a vertical carrier and a substantially horizontal holding device disposed on the vertical carrier, said support for said spring being displaceably mounted on the substantially horizontal holding device.

7. The copy milling device according to claim 6, which comprises a fixing device with at least two mutually crossing linear guides for fixing said support on said holding device.

8. The copy milling device according to claim 6, which comprises a holding device for said support connected to said carrier pivotally about the longitudinal axis of said carrier.

9. The copy milling device according to claim 8, wherein a vertical spacing of said holding device from said carrier plate is between 15 cm and 60 cm.

10. The copy milling device according to claim 9, wherein said vertical spacing is approximately 35 cm.

11. The copy milling device according to claim 1, wherein said spring has a spring constant of between 5 N/m and 10 N/m.

12. The copy milling device according to claim 11, wherein the spring constant of said spring is approximately 7.3 N/m.

13. The copy milling device according to claim 1, which comprises a base plate rotatably mounted about a vertical axis and supporting thereon said arm with said machining tool and said tracing device being pivotably mounted both horizontally and vertically, said arm forming a pantograph with a transmission ratio of approximately 1:0.8, and wherein a carrier is rotatably supported on said base plate and said carrier includes a holding device supporting thereon the support of the spring, and wherein said carrier plate is mounted rotatably about a horizontal axis and on which disk-shaped holding elements are each arranged rotatably about a respective vertical axis, for receiving at least one shaping blank and the model body.

14. The copy milling device according to claim 1, comprising a suction removal device for removing dust produced upon machining of the shaping blank.

15. A copy milling device for milling workpieces, comprising:
    a carrier plate for a model body and a shaping blank;
    a motor-driven machining tool for machining a workpiece from the shaping blank and a tracing device for tracing the model body, said machining tool and said tracing device being mechanically and synchronously movably connected; and
    a suspension device for an arm on which the machining tool and tracing device are mounted, said suspension device including a spring for compensating for the weight of the arm, said spring connecting said arm and a support that is mounted so as to be horizontally movable relative to the carrier plate;
    wherein said motor-driven machining tool is disposed or disposable for access by a user in a condition of use and including a gripping element for varying a position of said machining tool and said tracing device.

16. The copy milling device according to claim 15, wherein said machining tool and said tracing device are connected through a mechanical connection including a step-up or step-down mechanism.

17. The copy milling device according to claim 16, wherein said step-down or step-up mechanism is formed by a pantograph.

18. The copy milling device according to claim 16, wherein a step-down ratio from said machining tool to said tracing device is between 1:0.9 and 1:0.7.

19. The copy milling device according to claim 18, wherein the step-down ratio is about 1:08.

20. The copy milling device according to claim 16, wherein a step-down or step-up ratio between said machining tool and said tracing device is variable.

21. The copy milling device according to claim 20, wherein the step-down or step-up ratio is variable in steps.

22. The copy milling device according to claim 15, wherein said arm is pivotally supported about a vertical axis.

23. The copy milling device according to claim 15, wherein said carrier plate for the model body and the shaping blank is rotatably supported about a substantially horizontal axis.

24. The copy milling device according to claim 23, wherein a position of said carrier plate is variable in steps.

25. The copy milling device according to claim 23, wherein the carrier plate is rotatably supported through an angle of 360. degree.

26. A copy milling device for machining workpieces, the device comprising:
- a carrier plate for a model body and a shaping blank;
- a motor-driven machining tool for machining a workpiece from the shaping blank and a tracing device for tracing the model body, said machining tool and said tracing device being mechanically and synchronously movably connected;
- a suspension device for an arm on which the machining tool and tracing device are mounted, said suspension device including a spring for compensating for the weight of the arm, said spring connecting said arm and a support that is mounted so as to be horizontally movable relative to the carrier plate in a longitudinal direction of the arm; and
- a holding element for mounting at least one of the model body and the shaping blank in said carrier plate.

27. The copy milling device according to claim 26, wherein said holding element is disk-shaped and made of plastic material, and said model body is glued into a receiving opening formed in said disk-shaped holding element of plastic material, and an outline of said receiving opening is adapted to a contour of the model body.

28. The copy milling device according to claim 27, wherein the receiving opening in said holding element is a machined opening.

29. The copy milling device according to claim 26, wherein said machining tool has a milling element and said tracing device has a tracing element.

30. The copy milling device according to claim 29, wherein said milling element and said tracing element correspond in shape, at least in the portions wherein they come into contact with the model body and the shaping blank, respectively, and wherein the portion of said milling element is proportionally larger, between 10% and 40%, than the portion of said tracing element.

31. The copy milling device according to claim 30, wherein said portion of said milling element is about 25% proportionally larger than said portion of said tracing element.

32. The copy milling device according to claim 29, wherein said milling element and said tracing element are formed with tips being substantially trapezoidal in cross-section, and having a taper towards a shank thereof.

33. The copy milling device according to claim 26, wherein said copy milling device includes a carrier with a supporting element for said arm and/or magnets for releasably fixing said arm to said carrier disposed in said arm and in said carrier.

34. The copy milling device according to claim 26, which comprises a base plate and a rotary mechanism disposed on an underside of said base plate and configured to rotate the copy milling device about a vertical axis.

35. The copy milling device according to claim 34, wherein said rotary mechanism includes a rotary fitment.

36. The copy milling device according to claim 35, wherein said rotary mechanism includes at least one braking element.

37. The copy milling device according to claim 26, wherein the model body and/or the shaping blank can be or are rotatably disposed in said carrier plate.

38. The copy milling device according to claim 26, wherein the holding element comprises a disk-shaped holding element for mounting the model body and/or the shaping blank in said carrier plate.

39. A copy milling device comprising:
- a carrier plate for supporting a model body and a shaping blank, the carrier plate having at least one through opening formed therein configured to allow dust produced when milling the shaping blank to pass therethrough;
- a motor-driven machining tool for machining a workpiece from the shaping blank and a tracing device for tracing the model body, said machining tool and said tracing device being mechanically and synchronously movably connected; and
- a suspension device for an arm on which the machining tool and tracing device are mounted, said suspension device including a spring for compensating for the weight of the arm, said spring connecting said arm and a support that is mounted so as to be horizontally movable relative to the carrier plate in a longitudinal direction of the arm.

40. The copy milling device according to claim 39, wherein the carrier plate is formed with an opening adapted to receive the shaping blank.

41. The copy milling device according to claim 39, wherein a holding element can be releasably fixed to the carrier plate, and wherein the holding element is formed with an opening for the shaping blank.

42. The copy milling device according to claim 41, wherein the holding element is fixed to the carrier plate by two-part inserts.

43. The copy-milling device according to claim 41, wherein the at least one through opening is formed in the holding element.

44. The copy-milling device according to claim 41, wherein the holding element has a circular peripheral edge.

45. The copy milling device according to claim 41, wherein the holding element is a ring which is traversed by two limbs in such a way that an inner region of the ring has three openings.

46. The copy milling device according to claim 39, wherein the model body serves as a pattern for the shaping blank to be machined.

47. The copy milling device according to claim 39, wherein the carrier plate includes a releasable holding element that has a receiving means for a shaping blank and a through opening.

48. The copy milling device according to claim 39, wherein the carrier plate is supported for rotation about a horizontal axis.

49. The copy milling device according to claim 39, wherein said carrier plate includes a disk-shaped holding element.

50. A copy milling device for the production of dental workpieces, comprising:
- a base plate, a carrier plate for a model body and a shaping blank,
- an arm arranged pivotably with respect to a horizontal axis, said axis extending substantially normal to a longitudinal direction of said arm and said arm having a motor-driven machining tool for cutting shaping of a workpiece from the shaping blank and a tracing device,
- said machining tool and said tracing device being mechanically and synchronously movably connected,
- wherein said model body and said shaping blank can be or are arranged in through openings of said carrier plate by means of disk-shaped holding elements,
- said holding elements each having a through opening for accommodating said model body and said shaping blank, respectively.

* * * * *